(12) United States Patent
Delk et al.

(10) Patent No.: US 7,632,248 B2
(45) Date of Patent: *Dec. 15, 2009

(54) SURGICAL IRRIGATION SYSTEM

(75) Inventors: Michael Delk, North Kingstown, RI (US); Augustus Felix, Cranston, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 615 days.

This patent is subject to a terminal disclaimer.

(21) Appl. No.: 10/380,143

(22) PCT Filed: Sep. 21, 2001

(86) PCT No.: PCT/US01/29719

§ 371 (c)(1),
(2), (4) Date: Jun. 17, 2003

(87) PCT Pub. No.: WO02/24252

PCT Pub. Date: Mar. 28, 2002

(65) Prior Publication Data

US 2004/0097872 A1    May 20, 2004

Related U.S. Application Data

(60) Provisional application No. 60/234,555, filed on Sep. 22, 2000.

(51) Int. Cl.
*A61M 1/00* (2006.01)
(52) U.S. Cl. .................................... 604/151

(58) Field of Classification Search ............. 604/30–33, 604/151–153, 27, 29, 246–249, 254
See application file for complete search history.

(56) References Cited

U.S. PATENT DOCUMENTS 4,003,255 A * 1/1977 Spencer .................... 73/861.71
4,808,167 A * 2/1989 Mann et al. ................. 604/151

(Continued)

FOREIGN PATENT DOCUMENTS

DE    1906029    8/1970

(Continued)

*Primary Examiner*—Kevin C Sirmons
*Assistant Examiner*—Bhisma Mehta
(74) *Attorney, Agent, or Firm*—Leason Ellis LLP

(57) ABSTRACT

A surgical irrigation system comprises a reusable console and a disposable pump unit. The disposable pump unit includes a pump/motor module which includes a pump and a motor for driving the pump. The module is adapted to be mechanically supported within a seat in the console. The console produces a direct voltage at a pair of terminals within the seat. When the pump/motor is placed within the seat, the console terminals are connected to contacts on the module to provide a source of direct voltage for the pump motor. In the preferred embodiment, the disposable unit includes a handpiece and an irrigation valve. A flow sensing device within the outlet tube if the pump/motor module is actuated when the valve is open to turn the motor on and drive the pump. When the valve is closed, the flow sensing device turns the motor off.

24 Claims, 11 Drawing Sheets

U.S. PATENT DOCUMENTS

| | | | |
|---|---|---|---|
| 5,078,683 A * | 1/1992 | Sancoff et al. | 604/67 |
| 5,142,271 A * | 8/1992 | Bailey et al. | 340/606 |
| 5,484,402 A | 1/1996 | Saravia et al. | |
| 5,807,313 A * | 9/1998 | Delk et al. | 604/35 |
| 5,810,770 A | 9/1998 | Chin et al. | |
| 6,176,847 B1 | 1/2001 | Humphreys, Jr. et al. | |
| 6,436,072 B1 * | 8/2002 | Kullas et al. | 604/151 |
| 6,685,667 B1 * | 2/2004 | Delk et al. | 604/30 |
| 7,001,365 B2 * | 2/2006 | Makkink | 604/254 |

FOREIGN PATENT DOCUMENTS

| | | |
|---|---|---|
| WO | WO 95/23627 | 9/1995 |
| WO | WO 01/51105 A2 | 7/2001 |

\* cited by examiner

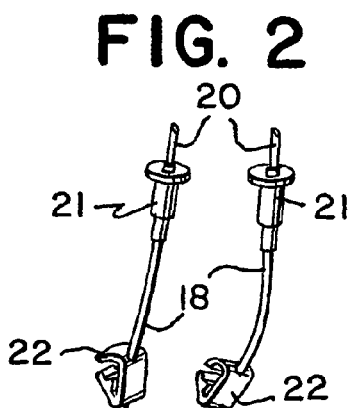
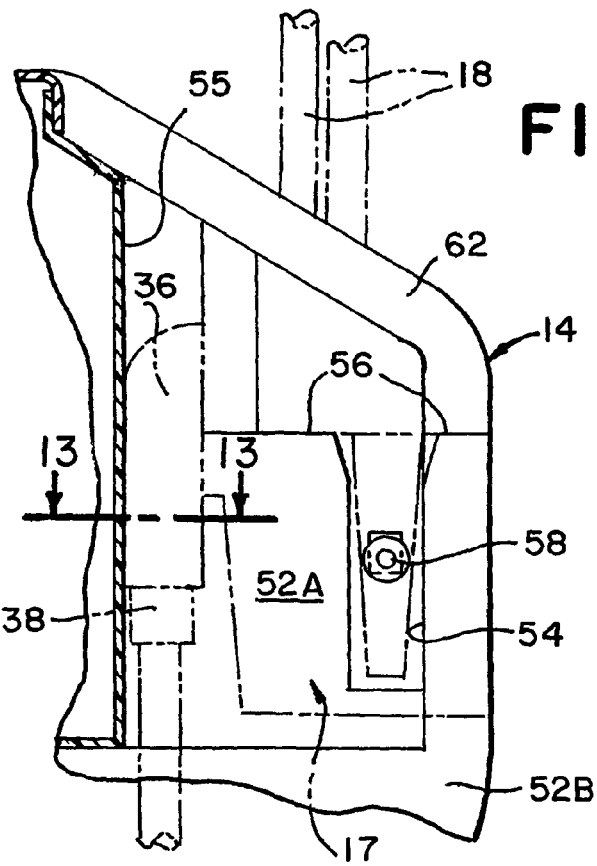
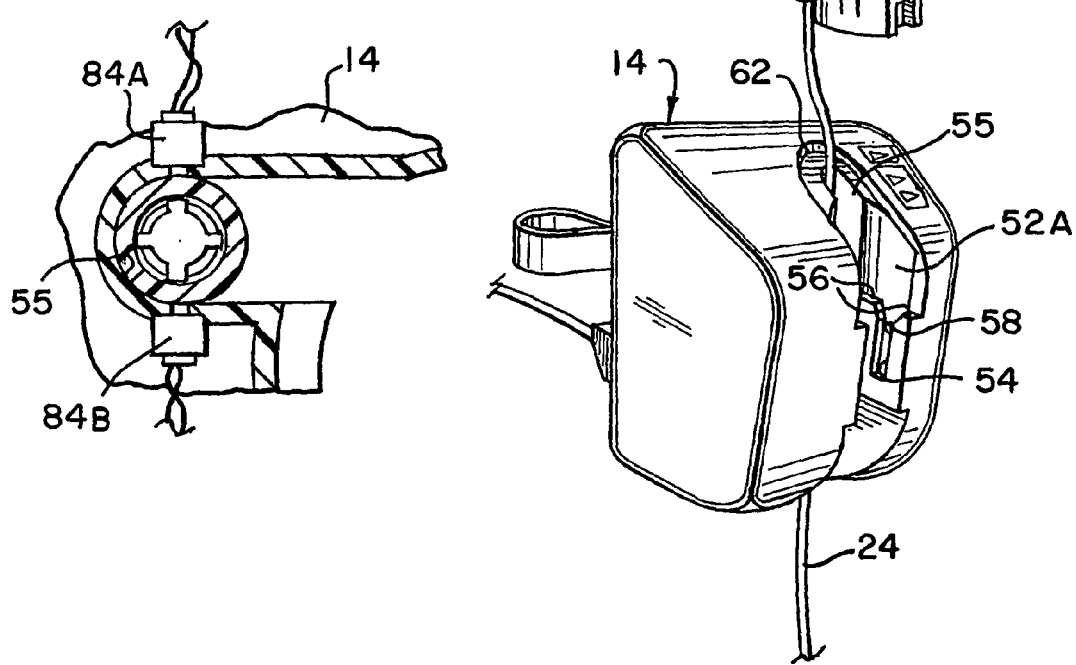

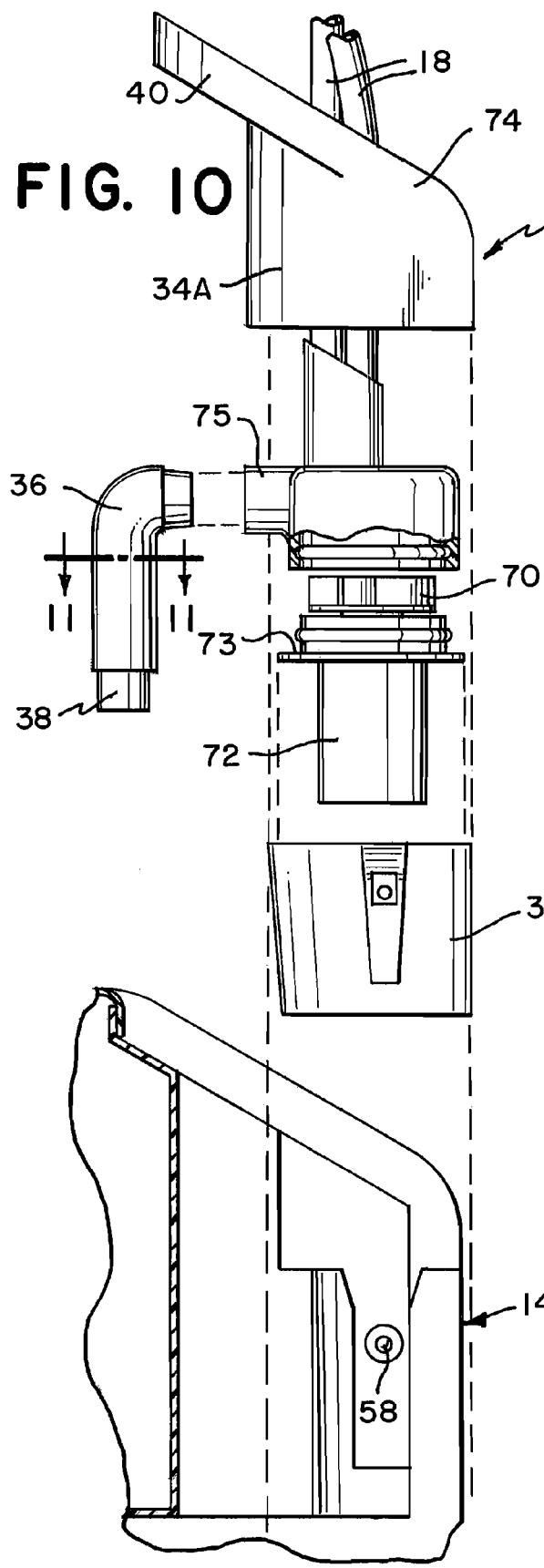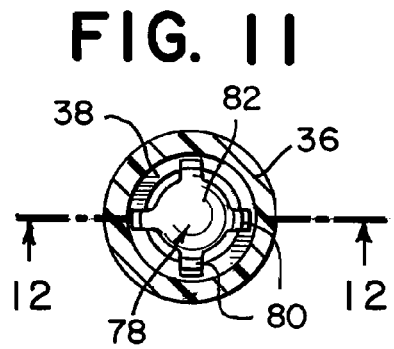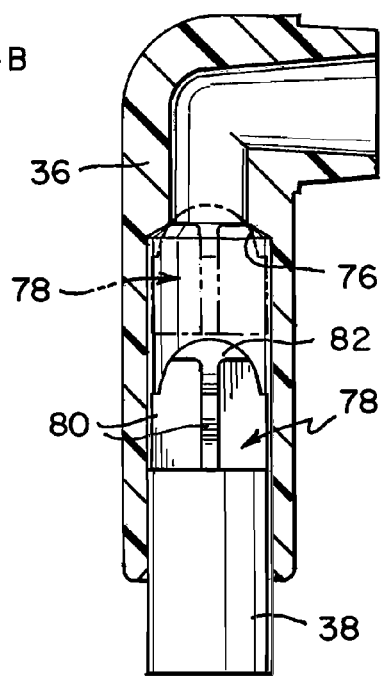

SURGICAL IRRIGATION SYSTEM

This application is a 371 of PCT/US01/29719, filed Sep. 21, 2001, which claims priority under 35 U.S.C. §119 from provisional application Ser. No. 60/234,555, filed Sep. 22, 2000 and entitled "Surgical Irrigation System".

This invention relates to surgical irrigation systems and, more particularly, to a surgical irrigation system particularly well suited for laparoscopic surgery.

BACKGROUND OF THE INVENTION

The development of minimally invasive endoscopic surgery has resulted in a proliferation of different surgical irrigation systems. Some irrigations systems have been developed for one particular type of surgery, e.g. laparoscopic surgery as opposed to arthroscopic or hysteroscopic surgery. Other irrigation systems have been developed which include reusable and relatively costly consoles which cooperate with a disposable unit tailored for a particular surgical application.

Fundamentally, there are three principal criteria for manufacturing irrigation systems. First, the system must be easy to set up and use in the operating room. Secondly, it must provide the required pressure and flow rates. In the case of laparoscopic surgery, surgeons sometimes use a relatively high pressure flow of irrigation liquid to separate tissues (hydro-dissection); however, excessive pressure may be undesirable if the objective is simply to irrigate a surgical site. The third criterion is cost which, for obvious reasons, is a major consideration today.

The early irrigation systems were simple gravity fed devices and, later, "bag squeezers". A bag squeezer applies pressure to the bag which contains the irrigation liquid. While the bag squeezer has the benefit of a relatively inexpensive disposable, the mechanism for squeezing the bag is relatively expensive. Moreover, conventional bag squeezers require air flow for operation and not all operating rooms have an available supply of air. The pressure provided by a bag squeezer is reasonable but it is limited by the strength of the bag which contains the irrigation liquid. An irrigation system manufactured and sold by Davol under the trademark Endo-Flo is also widely used. In the Endo-Flo irrigation system, a pump is driven by a diaphragm which is vibrated by a flow of air to pump irrigation fluid. This device is relatively inexpensive but it too requires a source of air, which is not always available.

Battery driven surgical irrigators have also been used. Representative examples of battery powered irrigators are shown in U.S. Pat. Nos. 5,484,402 and 5,807,313. These devices are convenient to use and produce a reasonable pressure, but they are expensive to manufacture. A number of devices are also known in which a disposable cartridge or cassette cooperates with a reusable console. For the most part, however, these systems require relatively expensive consoles and are not simple to set up and use in the normal operating room environment.

Objects Of The Invention

The object of the invention is provide an improved surgical irrigation system which satisfies the three criteria described above.

A more specific object of the invention is to provide an irrigation system which is virtually foolproof insofar as its installation is concerned and, in addition, relatively inexpensive insofar as the capital cost for the reusable component and the cost of the disposable are concerned.

SUMMARY OF THE INVENTION

In accordance with the invention, a surgical irrigation system includes a reusable console and a disposable pump unit. The disposable pump unit includes a pump/motor module, a handpiece, and tubing which connects the pump/motor module to the handpiece and to the irrigation bag. The console is adapted to be plugged into a conventional 110 volt ac source and converts the ac source to direct voltage for driving the pump motor. In accordance with the invention, insertion of the pump/motor module into the console automatically connects the motor to the direct voltage in the console. Both the console and the disposable pump unit can be made relatively inexpensively, and since 110 volt ac is conveniently available in all operating rooms the irrigator is easy to set up and use. The arrangement further can provide high direct voltages for driving the motor at virtually no increase in cost which means that it is a simple matter to provide increased pressure when desired for hydro-dissection.

IN THE DRAWINGS

FIG. 2 is a perspective view showing a reusable controller and disposable pump assembly in accordance with the preferred embodiment of the invention;

FIG. 9 is a sectional view similar to FIG. 6 showing the position of the pump/motor module in phantom lines;

FIG. 10 is an exploded side plan view partially in section showing the contents of the pump/motor module;.

FIG. 11 is a top sectional view along the line 11-11 of FIG. 10;

FIG. 12 is a side sectional view along the line 12-12 of FIG. 11;

FIG. 13 is a top sectional view along the line 13-13 of FIG. 9;

DETAILED DESCRIPTION

Figure 1:
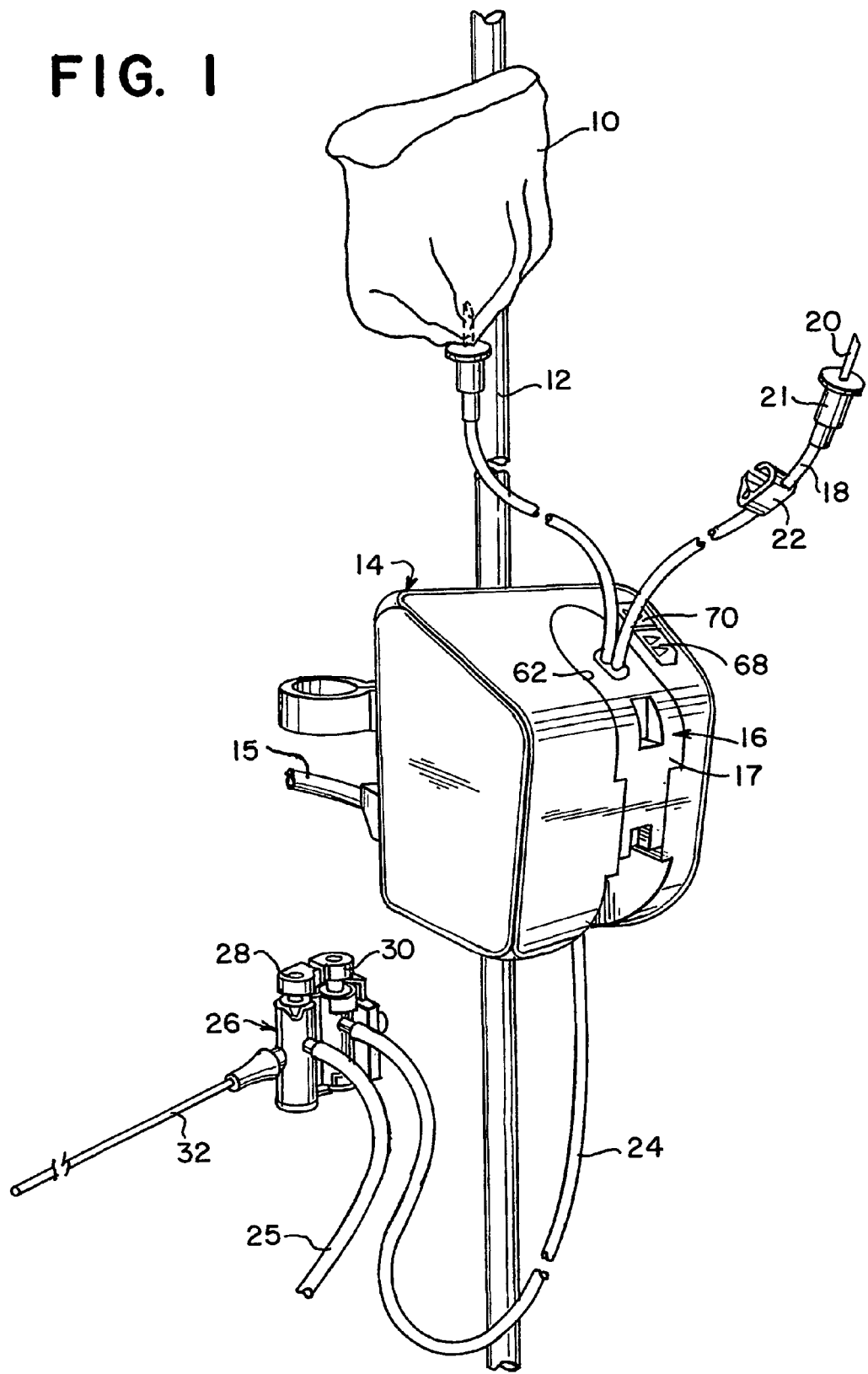
FIG. 1 is a perspective view of an irrigation system in accordance with a preferred embodiment of the invention.

FIG. 1 shows the main components of a surgical irrigation system in accordance with a preferred embodiment of the invention.

A standard irrigation bag 10 is supported on an IV pole 12 (or other device such as a cart) in conventional fashion. Only one irrigation bag is illustrated although frequently two irrigation bags are employed. A console 14 is also supported on the IV pole 12. The console 14 may be connected to a standard 110 volt ac wall outlet by a wire 15. Console 14, which is reusable, provides a physical support for a disposable pump unit 16.

The disposable pump unit 16 includes a pump/motor module 17, and two inflow tubes 18 which terminate in conventional spikes 20 so that the pump unit can be connected to one or two irrigation bags 10. A one-way valve 21 is situated immediately beneath each of the spikes 20 and, as described below, functions to permit liquid to flow from the irrigation bags to the module 17, but prevents the flow of liquid back into the bags. A clamp 22 is provided in each inflow tube 18. The disposable pump unit 16 also includes an irrigation outlet tube 24, a suction tube 25, and a handpiece 26 connected to tubes 24 and 25. Handpiece 26 may be conventional and includes trumpet valves 28 and 30 for applying suction or irrigation liquid to a wand 32 which can be extended to the operating site during use. When the valve 28 is depressed with tube 25 connected to a vacuum source, suction is applied at the operating site and when valve 30 is depressed, irrigation liquid is applied. As described more fully below, the pump/motor module 17 contains a motor, an impeller, and a shutter (not shown in FIGS. 1-9) which enable liquid to be pumped from the irrigation bags 10 to the outlet tube 24 when the trumpet valve 30 is depressed.

In the preferred embodiment, the console functions as a dc power supply and includes a transformer T (FIG. 6) which converts standard 110 volt ac to low voltage direct current suitable to drive a dc motor. By controlling the amount of voltage delivered to the motor, the user can control flow output levels. Instead of using a transformer based power supply, the console could include rechargeable batteries and a transformer for recharging the batteries, or the transformer could be a separate unit. The motor could run off of the transformer or the batteries so that if ac power were not available or inconvenient, the pump could be driven by battery power.

As shown in FIG. 2, the pump/motor module 17 is shaped to fit into a complementary seat within the console 14. When the module is placed into the console 14, the console provides a stable mechanical seat for the module and also electrically connects the motor within the module to terminals on the console which provide the direct voltage required to actuate the motor.

Figure 8:
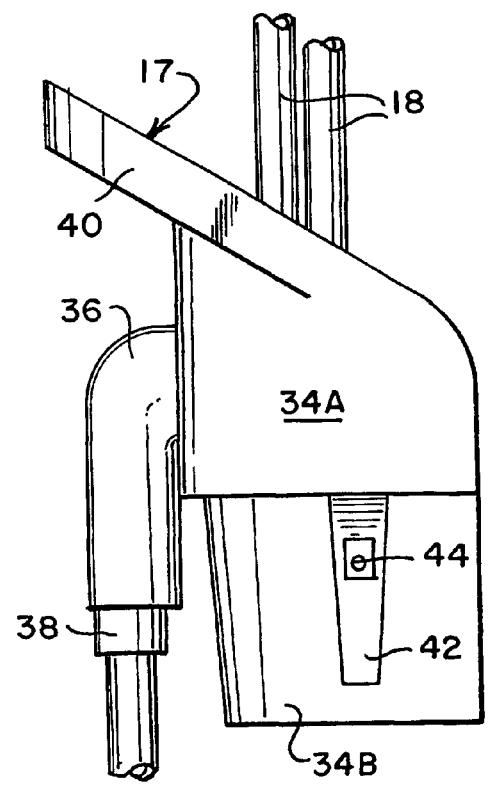
FIG. 8 is a side plan view of the disposable pump unit.

The module 17 includes an upper housing 34A and a lower housing 34B (FIG. 8). As explained below with reference to FIGS. 10-12, the upper housing 34A contains the impeller and the lower housing 34B contains the motor. Housing 34A also includes an elbow 36 and sleeve 38 through which liquid from the pump flows to the outlet tube 24. A slanted cap 40 extends from the upper housing 34A and fits flush with the upper surface of console 14 when the module 17 is seated within the console.

A protrusion in the shape of a ramp 42 extends from each side of the lower housing 34B, and an electrical contact 44 is spring biased outwardly from each of the ramps 42. The contacts 44 are electrically connected to the motor terminals and, as described below, adapted to electrically engage terminals within the console 14 so that direct voltage from the console can be applied to the motor within the housing.

Figure 6:
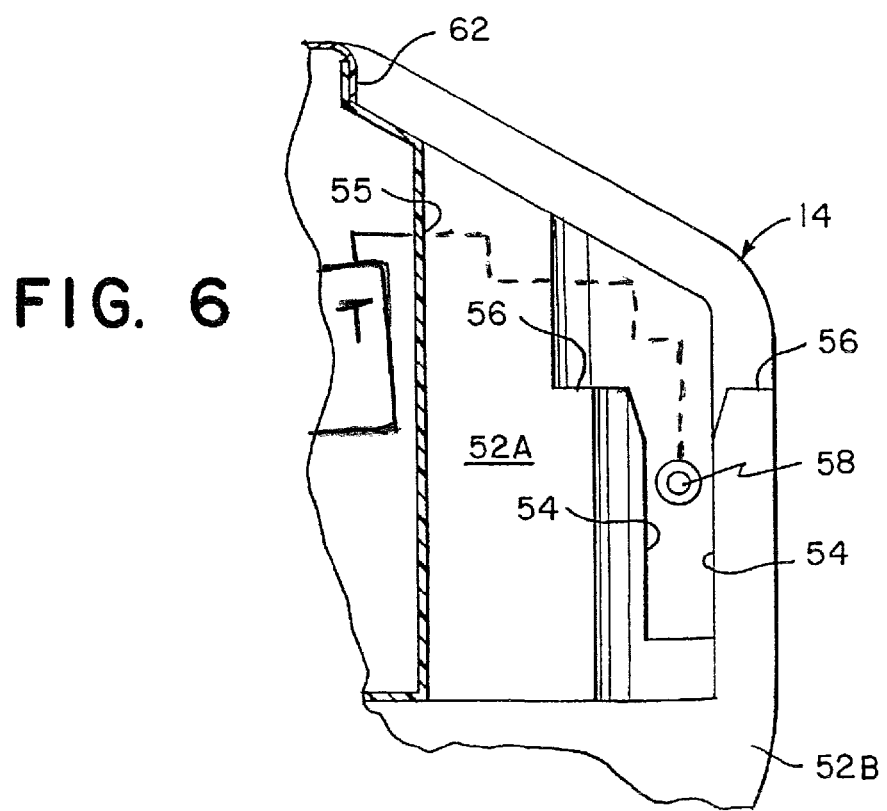
FIG. 6 is a sectional view along the line 6-6 of FIG. 3.
Figure 7:
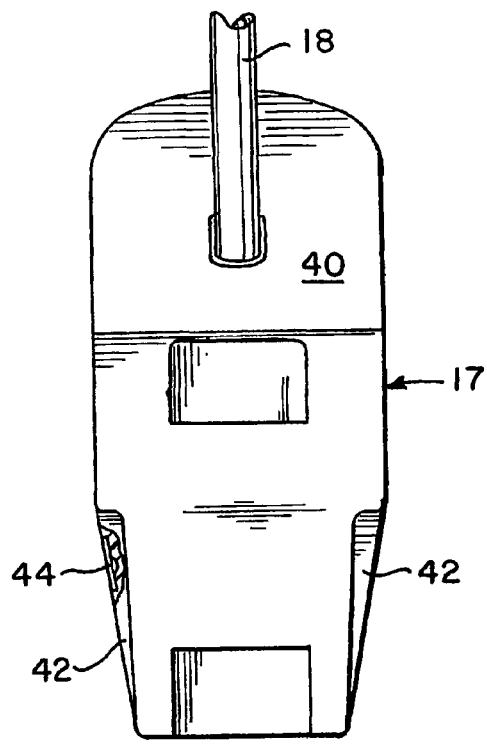
FIG. 7 is a front plan view of a disposable pump unit in accordance with a preferred embodiment of the invention.

Viewed from the top (see FIG. 3) console 14 is bifurcated to form a cavity 52 in which the module 17 can be seated in only one orientation with the outlet tube 24 extending from the bottom of the console (see FIG. 1). The cavity 52 includes an upper seat 52A and a lower seat 52B which retain the upper module housing 34A and lower housing 34B, respectively. Opposing longitudinal recesses 54 are provided in the lower seat 52B for receiving the ramps 42. This prevents forward and rearward motion of the module. As shown in FIG. 6, the longitudinal recesses allows for insertion of the module 17 within the console in only one orientation. A longitudinal passage 55 is provided to receive the elbow 36 and sleeve 38 which contain the flow sensing device as described below. As shown in FIGS. 2 and 9, the outlet tube 24 is disposed within and passes through the longitudinal passage 55. Circular terminals 58 extend into the recesses 54 to couple the direct voltage produced within the console 14 to the contacts 44 on the pump/motor module 17 to power the motor when the housing is seated in the console. Shelves 56 at the top of the recesses 54 provide vertical support for the undersurface 60 of the upper housing 34A. The shelves 56 are located intermediate the ends of the cavity 52 and are located at entrances to the recesses 54. A slot 62 in the upper surface of console 14 receives the top cap 40 of the housing 34. As shown in FIGS. 1 and 2, the cavity 52 is open along a top and a side of the console 14 and is configured to enclose only three sides of the module 17, while a front side of the module 17 is exposed when the module 17 is seated. The cavity 52 is also defined by a console floor shown in FIG. 3 and an upper surface of the console 14 on which the cap 40 rests when the module 17 is seated within the console 14.

As shown in FIG. 6, each of the recesses 54 is slightly V-shaped at its upper end to facilitate movement of the ramps 42 on the pump/motor module 17 into the console recesses 54.

Figure 3:
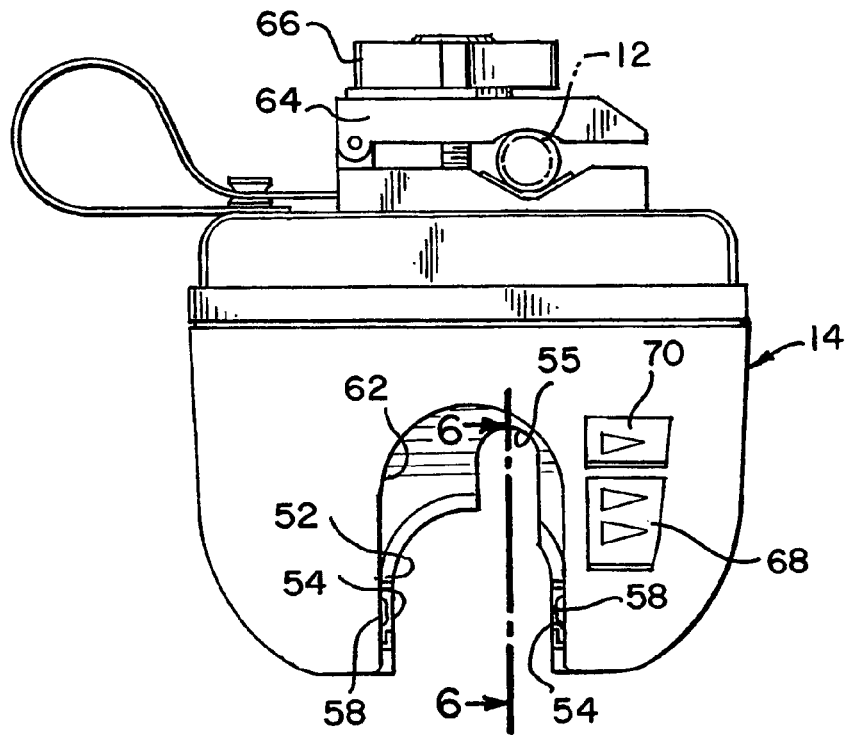
FIG. 3 is a top plan view of the controller.
Figure 4:
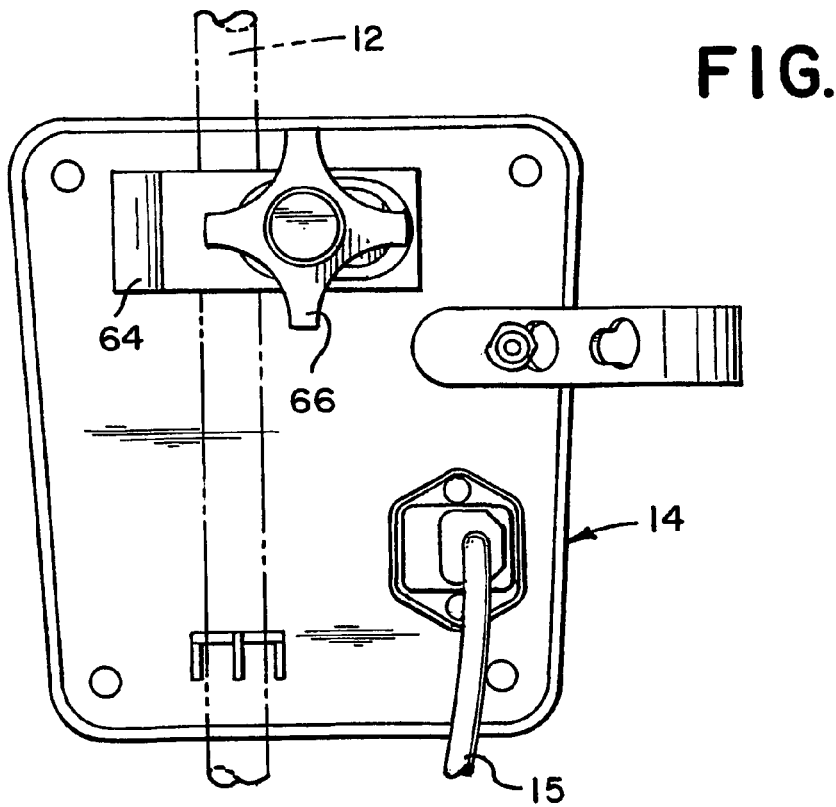
FIG. 4 is a rear view of the controller.
Figure 5:
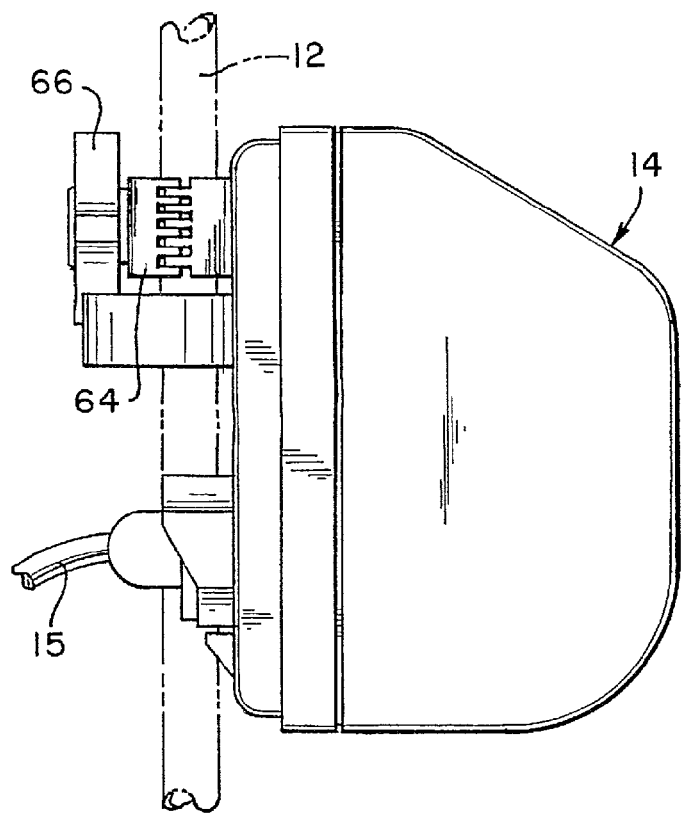
FIG. 5 is a side view of the controller clamped to an IV pole.

The console 14 can be secured to the IV pole 12 by means of a conventional clamp 64 which can be tightened or loosened by knob 66. As shown in FIG. 3, the console also includes lighted dome switches 68 and 70 which enable the operator to select the voltage applied by the console to the motor. The pump pressure is changed by varying the direct voltage applied by the console to the pump/motor module 17 as explained above. It is also possible to control the speed of the motor from a remote location. To do this, the control unit would include a portal for receiving a plug-in remote module. When plugged into the console 14, the module would bypass the motor speed control circuit in the console. It would be connected by electrical wires to a switch which typically would be positioned in a sterile field, for example by clipping the switch to a drape. The surgeon could then change the motor speed (and thus pressure) by actuating the switch in the sterile field. The current carrying capacity of the wires and switch can be low because they are connected to the logic circuit and not to the motor.

The details of the pump/motor module 17 are shown in FIGS. 10-12. The combination of the impeller, motor and flow sensor used in the preferred embodiment is very much like the corresponding elements illustrated and described in U.S. patent application Ser. No. 09/481,120 filed on Jan. 11, 2000, and entitled Electrically Powered Surgical Irrigator and that application is hereby incorporated by reference into this specification. The pump comprises a rotatable impeller 70 which is driven by a motor 72. A water tight seal between the impeller and motor is provided by a deck 73 and suitable seals (not numbered). The two inflow tubes 18 are introduced into the top of a pump head 74 in which the impeller is situated. The pump head also includes a tangential outlet port 75 which is connected to the input side of elbow 36. Rotation of the impeller drives the water from the inlet tubing 18 through tangential outlet port 75, elbow 36 and sleeve 38 to the outlet tube 24.

The elbow 36 includes an enlarged diameter section or chamber 76 in which an opaque float or shutter 78 can move in response to liquid flow through the elbow. The shutter includes four fins 80 and an upper dome 82. The upper dome occludes the flow channel through elbow 36 when the shutter is in its uppermost position as shown in dotted lines. The finned construction permits liquid flow when the shutter is driven to its lowermost position shown in solid lines, at the upper end of sleeve 38.

Elbow 36 may be made of polycarbonate or any other material transparent to optical energy which, in the preferred embodiment, is infrared. The infrared transmitter 84A and receiver 84B are mounted in the reusable controller on a cradle (not shown) within console 14 on opposite sides of passage 55. A printed circuit board (not shown) which contains the electronic circuitry for sensing an interruption of the infrared beam by the shutter and for driving the motor may physically support the cradle, with the console terminals 58 connected to the printed circuit board. A suitable circuit for this purpose is shown in U.S. patent application Ser. No. 09/481,120. When the shutter 78 is in its uppermost position, i.e. when no liquid is flowing through elbow 36, the infrared beam passes from the transmitter 84A through a transparent window (not shown) in the console surface defining passage 55 and through the transparent elbow 36 to the IR receiver 84B. When valve 30 is depressed and flow starts, the shutter is pushed downwardly to the position shown in solid lines in FIG. 12 where it interrupts the infrared light beam. The interruption of the beam is sensed by the circuit on the printed circuit board which then closes the energizing circuit to the motor.

In the preferred embodiment, a one-way valve 21 is placed in each of the inlet lines 18 immediately beneath the spike 20. As explained below, the one-way valve enhances performance of the irrigator when used with an optical flow detector in a number of ways.

If there is no valve in the inlet line, when the surgeon releases the irrigation valve 30 in handpiece 26, the pressure in the system returns to the liquid head pressure and the liquid can flow back into the irrigation bag 10. This causes a slight delay between the time the irrigation valve 30 is next depressed and the time the powered irrigant stream reaches the surgical site. With the one-way valve 21, when irrigation valve 30 is released, the liquid within the pump system (between one way valve 21 and irrigation valve 30) is maintained at a pressure above the liquid head pressure. Thus, when irrigation valve 30 is depressed, the release of the stored energy moves the shutter 78 rapidly causing the pump to start operation almost immediately.

Furthermore, in endoscopic procedures where body cavities are distended (e.g. arthroscopy and hysteroscopy), it is desirable to maintain the distension when the pump is turned off from a lack of flow, for example if the outflow from the knee or uterus is stopped. By maintaining the pressure in the pump system above the pressure due to the liquid head, the distension is maintained when flow stops.

Another benefit of the one-way valve 21 is to prevent air bubbles within the system from affecting operation. Without the valve, as the pressure in the system tends to equilibrate when the irrigation valve 30 is released, air bubbles within the system will float upwardly toward the irrigation bag. As these bubbles pass the IR sensor, comprising IR transmitter 84A and IR receiver 84B (FIG. 13), they can unintentionally activate the motor. This is undesirable for a number of reasons. First, the surgeon expects the motor to turn off when the irrigation valve is not depressed. Secondly, the needless operation of the pump causes noise and can lead to overheating of the motor and unnecessary depletion of battery life (when battery power is used). With one-way valve 21 in the inlet line 18, when irrigation valve 30 is released, any air bubbles in the system are locked within the pressurized system; therefore, they are not subject to movement which would cause the motor to turn on.

Figure 14:
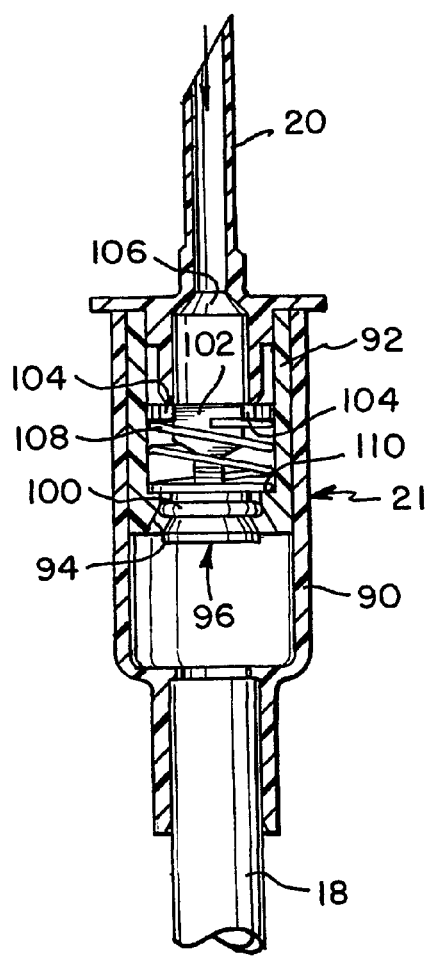
FIG. 14 is a side sectional view showing a preferred embodiment of a one-way valve in the closed position.
Figure 15:
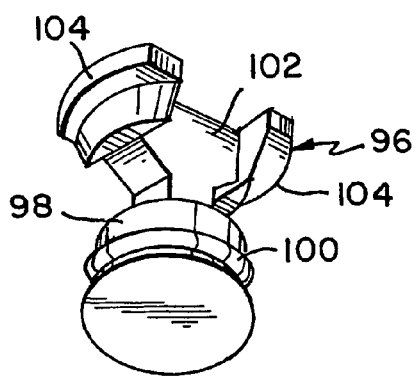
FIG. 15 is a perspective view of the valve body in accordance with a preferred embodiment.
Figure 16:
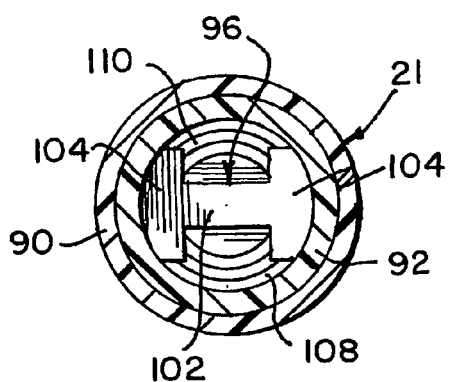
FIG. 16 is a sectional view along the line 16-16 of FIG. 14A.
Figure 17:
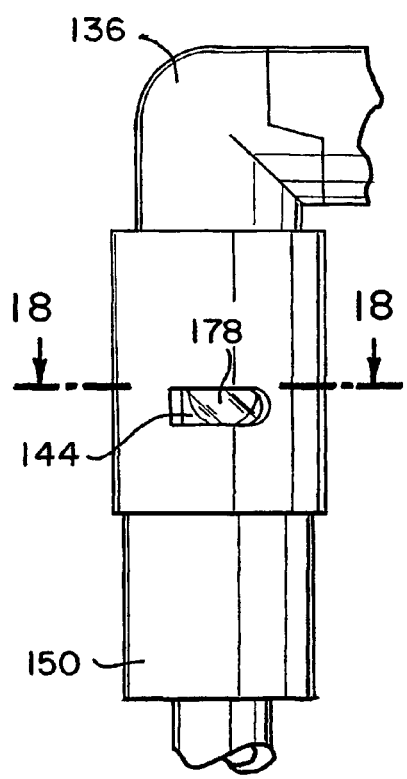
FIG. 17 is a side elevational view of the output fitting of the pump showing a second embodiment of a flow detection device which can be used to detect liquid flow when the irrigation valve is open.
Figure 18:
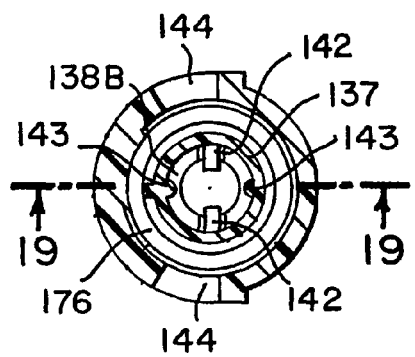
FIG. 18 is a cross sectional view along the line 18-18 of FIG. 17.

The construction of a preferred one-way valve 21 is shown in FIGS. 14-16. The valve includes an exterior cylindrical housing 90 which is attached to the spike 20 at its upper end and to the inlet tube 18 at its lower end. A cylindrical internal seat 92 is fixed in the upper portion of housing 90 and includes a conical surface 94 which flares outwardly at its bottom and serves as a seat for a valve body 96.

Valve body 96, as shown in FIG. 15, includes a generally cylindrical base 98 which is flared at its lower end so that a sealing O-ring 100 can be held on the base. A cross piece 102 extends upwardly from base 98 and includes two outwardly extending retaining lips 104. As shown in FIG. 16, the width of the cross piece 102 is less than the diameter of the spike conduit 106. A coil spring 108 is compressed between the under surfaces of the retaining lips 104 and the upper surface of an internal rim 110 from which the conical seating surface 94 extends. Spring 108 urges the valve body 96 toward the spike 20 which biases O-ring 100 against the seating surface 94 to close the valve.

Figure 14A:
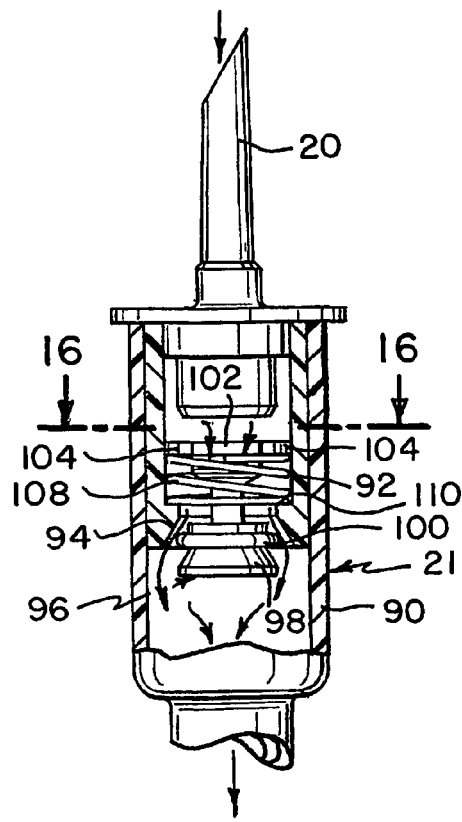
FIG. 14A is a side view partially in section showing the one-way valve in its open position.

When the irrigation valve 30 is closed, the valve body 96 is in the position shown in FIG. 14, i.e. valve 21 is closed. When the surgeon depresses valve 30, water starts to flow through spike 20 and conduit 106 due to gravity. The force applied by the water against the valve body 96 is greater than the retaining force applied by spring 108, causing the valve body to move downwardly to the position shown in FIG. 14A in which the irrigant flows past the O-ring 100 to the inlet tube 18. When irrigation valve 30 is released (i.e. closed), spring 108 returns the valve body to the position shown in FIG. 14 which closes the valve and prevents liquid from flowing upwardly through spike 20 into irrigation bag 10. This places the liquid in the pumping system under pressure. As a result, the motor is turned on almost immediately after valve 30 is depressed and the presence of air bubbles does not affect system operation.

Other types of flow sensing devices, such as pressure detectors and magnetic sensors can be used in place of the optical flow sensor. The motor also could be connected directly to the valve in the handpiece by electric conductors with a suitable switch in the handpiece to close the circuit when the valve is opened. The above mentioned U.S. Pat. Nos. 5,484,402 and 5,807,313 use handpiece switches which are connected to the motor by conventional wire. In both cases, the current required to drive the motor passes through the wire and switch. In accordance with this invention, wherein a reusable controller and disposable pump module are employed, the wire and switch can be relatively slight and, therefore, inexpensive because the current flowing through them is only needed to actuate the control logic in console 14.

Many power supplies can be used to drive the motor. In one embodiment, an off-the-shelf power supply manufactured by Condor D. C. Power Supplies, Inc. of Oxnard, Calif. (Medical-65 watt, 24 volt model GLN 65-24) was used. This device has two operating states. In the high voltage condition it produces 24 volts; in the low voltage condition it produces the equivalent of 18 volts which is achieved by applying the full 24 volts for approximately ⅔ of the time. The operator can select either the high or low voltage by touching switches 68 or 70, respectively. The invention contemplates any power supply with or without the ability to provide a variable voltage.

An interlock switch may be provided for safety purposes. For example, a switch (not illustrated) located at the bottom of the cavity 52 may be activated when the motor/pump module is properly loaded into the console. If the switch is not activated, the control circuit will not enable power to be transmitted to the terminals 58 in controller 14.

The device may also include a feature for automatically turning the pump off when the irrigation bag runs out of liquid. In this condition, the shutter 78 will be in the "flow" or lower-most position (FIG. 12). A low current, indicating an absence of fluid in the pump head, can be sensed and used to turn the motor off. The system is automatically reset during repriming when fluid refills the flow chamber and the shutter moves to the "no flow" or upper position.

In use, the pump/motor module is guided into the seating cavity in the controller and secured by a gentle push on the top. This connects the console terminals 58 to the module contacts 44. The bags are then spiked and the clamps on the inflow tubes released. To prime the system, the irrigation valve 30 is depressed until irrigant fills the flow switch chamber 76. With no liquid flowing, the shutter moves to the "no flow" (upper) position which "resets" the IR sensing circuit. When valve 30 is depressed again, the shutter moves to the "flow" position which turns the motor on to pump liquid through the tubing set. The system is then primed and ready for use.

When the procedure is complete, the pump/motor module is disengaged from the console by pushing upwardly on the bottom of the module.

Second Embodiment

A commercial version of the irrigator shown in FIGS. 1-16 incorporates features which are beneficial under certain conditions encountered in an operating room. These conditions are as follows.

First, when a surgical irrigation bag runs out of liquid, it is necessary to replace the used bag with a full bag and to reprime the pump. Repriming can be difficult since the liquid which remains in the irrigation line may contain air which impedes priming. Furthermore, depending on the height of the console on the IV pole, the resulting hydraulic head may not be sufficient to move the irrigation liquid through an upward leg of a draped tube. As a result, repriming may be slow or it may be necessary to force the liquid through the tubing, for example, by squeezing the irrigation bag.

Second, air bubbles which are trapped in the irrigation tubing can migrate into the float ball chamber. An air bubble may interrupt the IR beam which passes through the chamber and thus may cause the motor to run for brief periods of time. This can be disconcerting to the surgeon and may be construed as an indication of an intermittent fault.

Finally, the pump is designed for use with a variety of laparoscopic irrigation probes. The diameters of these probes differ considerably and, in the case of certain bipolar probes, can result in fluid flow which is so reduced that movement of the float ball when the irrigation valve is depressed is unacceptably slow, causing a delay in fluid delivery. This can prolong the surgical procedure and may disturb the surgeon. If the sensitivity of the system to flow is increased by reducing the distance the float ball must move to interrupt the IR beam, it becomes easier for the pump to be turned on inadvertently during handling of the tubing. Thus, there is a need to optimize the sensitivity of the pump so that its performance with restrictive tips is acceptable and the likelihood of a response to external influences other than depression of the irrigation valve is minimal.

The commercial embodiment of the invention provides solutions to each of the above mentioned problems. First, it provides a power assist, at the user's option, to the repriming procedure whereby the pump can be turned on to rapidly evacuate air from the disposable module.

Second, in the commercial embodiment, a float is used which, when it blocks the IR beam, causes the sensor to generate a voltage which is higher than the voltage generated when the IR beam is blocked by an air bubble. This enables the sensor to distinguish between the float and air which means that the motor can be responsive to the float alone.

Finally, because the console is a reusable item, it is economically feasible to provide a programmable device (IC) in the console which can control the operation of the pump in the disposable unit. The IC can be programmed to respond to the higher sensor output (referred to as an air immunity voltage) and then to switch to a lower voltage after a predetermined interval of time sufficient to ensure the evacuation of air from the disposable unit. In this way, the response time of the system can be improved without concern for the effects of air bubbles in the float chamber.

Mechanically, the commercial version of the invention is essentially the same as the device shown in FIGS. 1-16. Changes have been made in the flow sensing device and the key pad which controls the system operation. To the extent changes have been made, they are described below with reference to FIGS. 17-21.

FIGS. 17-20 illustrate the float chamber and ball used in the commercial embodiment of the invention. It functions the same way as the flow sensor shown in FIGS. 11-13 but its structure is different. It enables the sensor to distinguish between interruption of the IR beam by the float and by air bubbles and, therefore, serves an important role in avoiding the problems referred to above.

Figure 19:
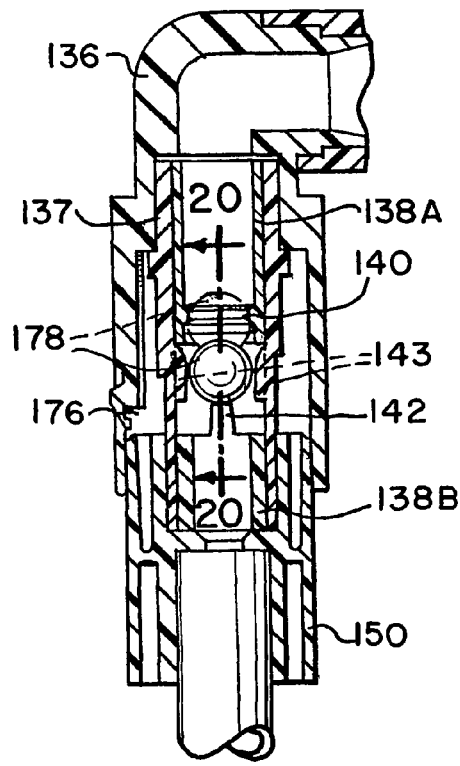
FIG. 19 is a side sectional view along the line 19-19 of FIG. 18.
Figure 20:
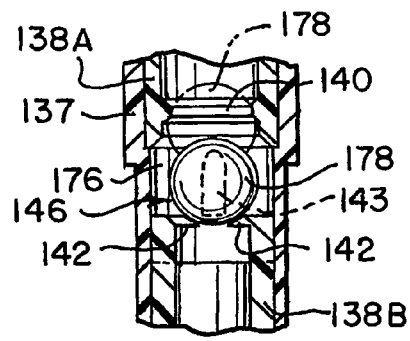
FIG. 20 is a sectional view along the line 20-20 showing the ball and flow chamber.

In FIGS. 17-20, the output of the pump passes through an elbow 136 which contains an outer sleeve 137 and upper and lower inner sleeves 138A and 138B, respectively. The upper inner sleeve 138A includes a ring 140 (FIG. 20) which limits the upward movement of the float, in this case, a ball 178. The downward movement of the ball is limited by two stop members 142 which extend upwardly from the lower inner sleeve 138B. In FIGS. 19 and 20, the lowermost position of ball 178 is indicated in solid lines and the uppermost position in dashed lines. A float chamber 176 may be considered to be the region between the upper ring 140 and lower stop 142. Two internal ribs 143 help to guide the ball.

The ball 178 is made of a material which is more opaque to IR radiation then air. For example, ball 178 may be made of black polypropylene.

The elbow 136 includes two diametrically opposed openings 144 (FIGS. 18 and 20) which allow the IR beam to pass through the float chamber 176 at location 146. Thus, when ball 178 floats (which only occurs when the float chamber is filled with water) the IR beam is not blocked. When the ball drops to its lowermost position (indicating either that liquid is flowing or that the float chamber is dry) the IR beam is blocked.

An annular connector 150 is adhered to the bottom of the elbow 136 between the inner surface of the elbow and the outer surface of the outer sleeve 137 and is connected to the outlet tube 24. The various parts shown in FIGS. 17-20 may be adhered together using suitable adhesives which are commonly used for medical devices of this type.

Repriming

Repriming is a serious concern since the inability to prime the system can be a major inconvenience. In the current embodiment, repriming can be achieved by gravity alone or by a power assisted priming feature using a key on the console keyboard.

Figure 21:
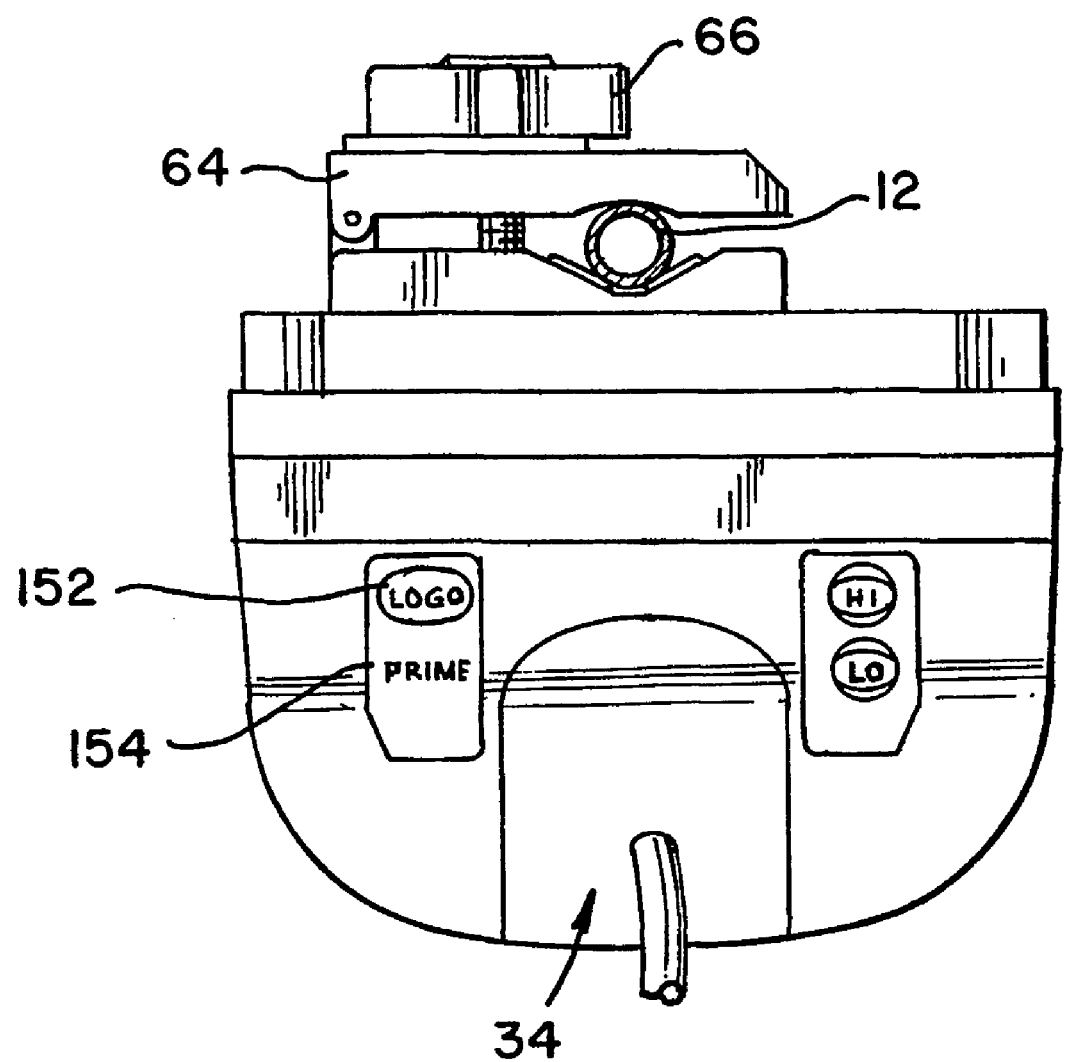
FIG. 21 is a top elevational view of the console according to a second embodiment of the invention illustrating a different configuration of control keys.

FIG. 21 illustrates the upper surface of the console in the commercial embodiment. It includes a keypad having two keys labeled HI and LO which replace switches 68 and 70 of the first embodiment. The HI and LO keys serve the same purpose, namely, to apply either a high voltage or a low voltage to the motor at the user's option. In the commercial embodiment, on the left hand side of the console, there are two visual displays 152 and 154 which represent a logo and the word "PRIME". Each display can be lit by an associated LED (not shown) which in turn can be actuated operated by the system controller. The HI and LO keys likewise have associated LEDs. The HI key also functions as a "power prime" key when the system is in a PRIME state. This means that the HI key can be pressed to start the motor to provide a power assist during priming.

Initial priming of the system is simple and relatively foolproof. Repriming, however, can be difficult because of the presence of air in the irrigation line and/or possible movement of the float ball due to handling of the controller or changing of an irrigation bag which can cause accidental transitions from one state to another. For example, a bouncing or oscillating ball can be perceived by the system as an indication that the system has been primed and is ready to run when the ball is down even though no fluid has entered the system. To avoid this problem, as described below, a predetermined delay is required for each transition made by the float ball if it is to be deemed "legal", i.e. as a float ball transition which is to have an effect on the system operation.

Figure 22:
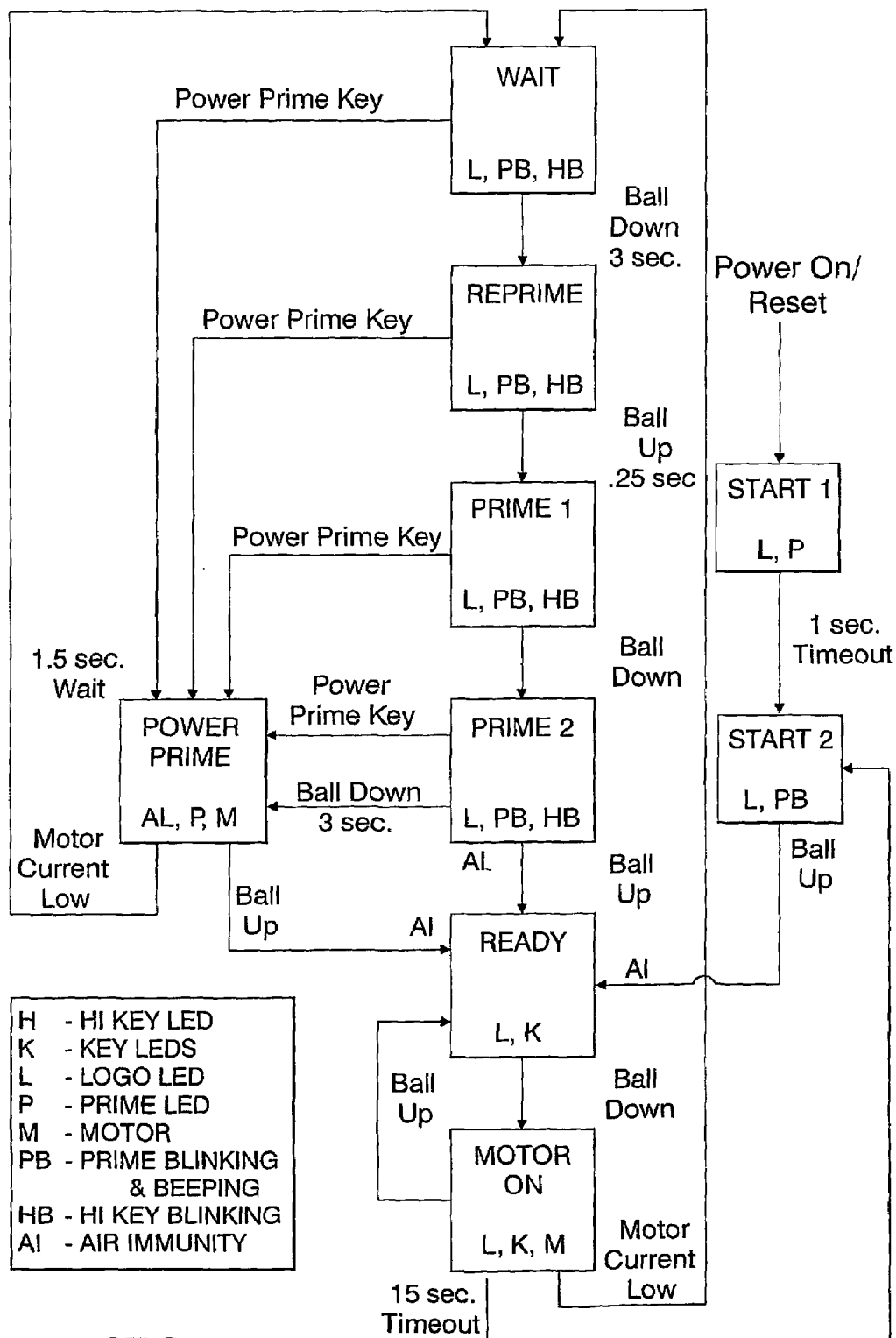
FIG. 22 is a diagram showing the various states of an irrigation system in accordance with the commercial embodiment of the invention.

The priming and repriming procedures are described below with reference to FIG. 22 which shows the various states of an irrigation system in accordance with the commercial version of the invention.

When the disposable pump/motor module is inserted into its seat within the console, the control system looks for three check points before enabling system operation. First, it looks for the closure of a magnetic proximity switch (not shown) which indicates that the pump/motor module has been properly installed in the console. Such proximity switches are well known and, therefore, the switch is not described or illustrated herein. If the switch is closed, the system goes into START. In that state, the control system applies a voltage to the contacts 58 on the console. It then checks to make sure that the "ball" is blocking the IR beam (an indication that the disposable unit is dry) and checks for continuity of the motor drive circuit which indicates correct installation of the motor. If any of these check points are not satisfied, a signal is provided (for example, a blinking logo) and the system will not proceed. If the check points are satisfied, after a one second delay, the system moves into START 2 in which the logo (DAVOL) LED is lit, the PRIME LED blinks, and the console emits an audible beeping tone.

If the ball is floating, indicating that the float chamber is filled, the system switches into a READY state in which the logo LED and both HI and LO key LEDs are lit. When the system is in the READY state, if the ball drops (indicating that liquid is flowing due to depression of the irrigation valve), the system then goes into the MOTOR ON state in which both the logo and HI and LO LEDs are lit and the motor is on. In the MOTOR ON state, if the ball floats to the up position, caused by closing the irrigation valve, the system returns to the READY state (with the motor off). If the motor runs for more than 15 seconds (for example) indicating possible continuous running due to poor priming or motor failure) the system reverts to the START 2 state in which the motor is off, the PRIME LED blinks and the console beeps. To restart the motor, the surgeon must release the irrigation valve causing the ball to return to its up position (if the system is properly primed) and the system to switch to the READY state.

In the MOTOR ON state, a third transition can occur when the motor current is low. If the irrigation bag no longer contains liquid, the current required to operate the pump will drop considerably. If the motor current is below a predetermined threshold (e.g. 1.1 amps) the system goes into a WAIT state in which the LED logo is lit, the PRIME LED blinks, the console beeps and the HI LED also blinks. This prompts the user that priming is necessary and that power priming (described below) by pressing the blinking HI key is available.

During repriming, the possibility exists that the ball may move when the handpiece and/or tubing is handled. To distinguish between unintended ball movement and intended ball movement, a system of legal transitions is established. In the commercial embodiment, a legal transition requires that the ball be down for three seconds, up for at least 0.25 seconds and then down again. Thus, when the surgeon, prompted by the blinking prime LED, presses the irrigation valve to prime the system, the ball moves down. If it stays down for three seconds, the system switches to a REPRIME state in which the same indicators are provided. If the irrigation valve is released, the ball floats to its up position. After 0.25 seconds, the system goes into a PRIME 1 state, again with the same indicators. When the irrigation valve is depressed again, the ball moves down and the system then goes into a PRIME 2 state with the same indicators. If the irrigation valve remains depressed for three seconds, the system then switches to the POWER PRIME state in which the logo and PRIME LEDs are lit and the motor is on. When the irrigation valve is released, if there is water in the float chamber, the ball floats to its upper position and the system goes into the READY state. If the motor current is low (e.g. less than 1.1 amps), the system returns to the WAIT state.

The priming process just described is controlled by the surgeon's use of the irrigation valve. The system is reprimed by depressing the valve twice. The system can also be reprimed by pressing the power prime key (the blinking HI key in the commercial embodiment) during the priming procedure. The depression of the power prime (HI) key for more than 1.5 seconds also places the system in the POWER PRIME state providing a motor assist to the priming procedure when the irrigation valve is depressed. This primes the system faster than is possible by gravity feed alone. After the system is primed, and the irrigation valve released, the ball floats to its upper position and the system is placed in the READY state. If, in the POWER PRIME state, the motor current is below the low threshold (e.g. 1.1 amps) indicating that there is no liquid in the irrigation bag, the system returns to the WAIT state.

There are other ways of enhancing repriming. For example, when the pump/motor module is properly installed in the console, the system may enter a PRIME state in which the motor immediately starts to run at a reduced background voltage (e.g. 5 volts) for a predetermined period of time (e.g. one hour). At that point, the background voltage can be discontinued and the system will wait to be gravity primed before entering the READY state. In the READY state, the motor will run at the background voltage for a programmed duration (e.g. four hours) after it was last used.

When low motor current is detected indicating a dry bag, the system will again run at the background voltage (5 volts) for an hour which will give an extremely long period of time in which to change bags while automatically providing a power assist to the user during repriming. In this case, the power assist repriming feature would be automatic. The pump running at this low voltage is barely audible and speeds up the response time for restricted flow probes such as the bipolar tip.

Air Immunity

As mentioned above, it is important that the pump not be turned on in response to an air bubble. This is a particular problem during repriming. It is also important that the system be able to respond relatively quickly even when the probe tends to restrict the flow of liquid (i.e. in the case of a bipolar tip).

In the commercial embodiment, when the IR beam is completely blocked (e.g. by steel), the output voltage of the sensor is three volts (voltage values herein obviously are exemplary). When the IR beam is blocked by an air bubble, the voltage output is 2.2 volts. Previously, the shutter was made of a red polypropylene material which was not entirely opaque to infrared and the sensor output voltage was 1.5 volts when the red shutter blocked the beam. In the commercial embodiment, the ball is made of a material which is more opaque to IR than air so that the output of the sensor when blocked by the ball is greater than the output if the IR beam is blocked by air. By way of example, the black polypropylene ball 178 will produce a sensor output of 2.8 volts when it is in the path of the IR, beam. Hence, the use of a black ball allows the ON/OFF threshold for the motor to be set substantially above the sensor voltage due to an air bubble (2.2 volts) which means that an air bubble is unable to turn the motor on even if it interrupts the IR beam.

The higher voltage (2.8 volts) may be deemed to be an "air immunity" voltage (the sensor is immune to air bubbles). When the threshold of the voltage detector is set to the air immunity voltage, the system will not be activated by an air bubble.

The output of the sensor is not a square wave; that is, it does not jump from 0 volts to 2.8 volts. Instead, there is a gradual increase in voltage as the ball approaches the IR beam. In the case of the restricted flow bipolar probes, response time can be improved by operating at a lower threshold voltage (1.5 volts, for example) rather than the air immunity threshold (2.8 volts). Operating at the lower threshold, however, would give rise to the possibility that the system may respond to air bubbles. In accordance with a further feature of the invention, during priming the motor is only capable of responding to a voltage which exceeds the sensor output due to an air bubble. After the motor is operated for a period long enough to ensure the removal of all air from the disposable pumping unit, the sensitivity of the system is increased so that it can respond to a lower sensor output voltage. Particularly in the case of bipolar probes, this enhanced sensitivity enables acceptable response times when the irrigation valve is depressed.

To accommodate both situations, the system controller is set so that whenever the system switches to the READY state from the START 2, PRIME 2 or POWER PRIME states, when the motor is turned on (by depression of the irrigation valve), for a predetermined period (e.g. 1 second) after the motor has been turned on, the system will only respond to the air immunity voltage (e.g. 2.8 volts). This gives the system time to clear any air bubbles from the pump (and float chamber) so that thereafter, the lower threshold voltage (1.5 volts) can be used without concern that the IR beam may be blocked by an air bubble. The designation "AI" in FIG. 21 means that this air immunity voltage is the threshold level of the IR sensor for a period of one second after the motor is turned on.

If the system is unused for an extended period when it is in a READY state, air may build up in the system over time. Therefore, in the commercial embodiment, the control system will reset the threshold voltage to the air immunity voltage (2.8 volts) whenever the system is in the READY state but unused for a predetermined period of time, for example two minutes. When this occurs, the sensor operates at the air immunity voltage but switches to the lower threshold sensor voltage (e.g. 1.5 volts) after the motor has run for a predetermined period of time sufficient to drive air from the flow chamber (for example, 0.25 seconds). This procedure will repeat each time the system is dormant in the ready state for the selected interval (two minutes).

Figure 23:
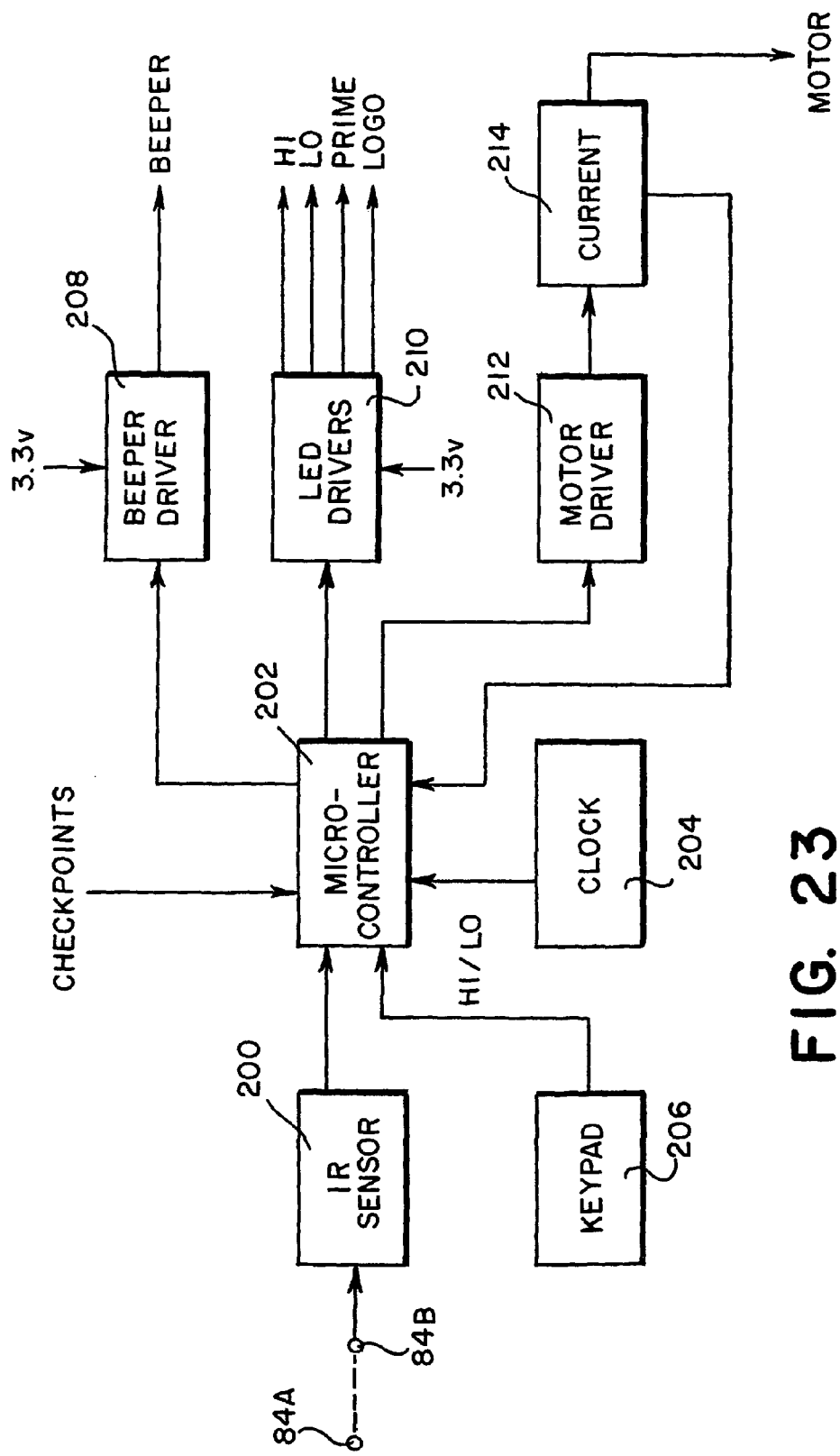
FIG. 23 is a block diagram showing the control circuit (logic) used to control the machine operation.

FIG. 23 is a block diagram of the control circuit within the console which controls the system operation. In FIG. 23, the IR transmitter 84A and IR receiver 84B cooperate with a sensor 200 which is mounted on a printed circuit board within the console for sensing the interruption of the IR beam. In the commercial embodiment, as explained above, the maximum output of the sensor when the IR beam is totally blocked may be 3 volts. An air bubble may produce a voltage of about 2.2 volts and the black ball 176 an output of 2.8 volts. The output of the sensor 200 is fed to a micro-controller 202 which may be a programmable integrated circuit (IC), for example, an EPROM. Microcontroller 202 is responsive to timing information from a clock 204 as well as signals from the HI/LO keypad 206.

The microcontroller 202 produces outputs which control a beeper driver 208, an LED driver 210 and a motor driver 212. The console also includes a voltage regulator (not shown) which produces the voltages necessary to drive the beeper, LED's and motor. Representative voltages are shown in FIG. 23.

In the case of the motor, high and low voltages (for example, 19 volts and 23 volts, respectively) can be coupled to the motor depending on whether the LO or HI key on the console is touched. The motor drive circuit also includes a device 214 for measuring the motor current. When the motor current drops below a predetermined threshold (1.1 amps in the example described) a signal is returned to micro-controller 202 which is programmed to operate the system as described above.

Various elements of the various embodiments of the resent invention may be characterized according to the function they perform. Examples include, but are not limited to those summarized in the table below:

| Means | Structure |
| --- | --- |
| Flow sensing means | The flow sensor |
| Means for converting an alternating current | Transformer |
| Cooperating elements which prevent lateral movement | the ramped protrusions 42 and recess 54. |
| Means for varying the voltage | Dome switches 68, 70 |
| A control circuit for selectively applying direct current | The control circuit |
| Means for mounting | Clamp 64 |
| Means responsive to current flow to the motor for turning the motor off | The control system. |

The invention claimed is:

1. A surgical irrigation system, comprising a reusable console and a disposable pump unit comprising a pump unit housing that is separate from the console and is insertable therein, said console including a transformer for producing a direct current, terminals on which a direct current from said transformer is produced, and a seat for mechanically supporting said pump unit after insertion of the pump unit into a cavity of the console, the seat shaped to substantially fit the pump unit housing and a wire operatively connected to the console, said pump unit including a pump/motor module including a pump, a motor for driving the pump, and an irrigation outlet tube that is operatively coupled to the pump to allow fluid to be transferred therethrough to a remote location, said pump unit housing containing said pump and motor, and contacts on said housing electrically connected to the motor, said housing being shaped so that when the pump unit is placed in said console seat, the pump unit is mechanically supported by the console and the console terminals are in electrical contact with the contacts on the pump unit housing connected to the motor, wherein the seat in the console includes a longitudinal passage for receiving the outlet tube and permitting the outlet tube to extend through and exit the console at a select location, the longitudinal passage being partially open along a longitudinal direction and open at a top of the console to allow lateral insertion of the outlet tube into the longitudinal passage and located so as to allow the pump unit to be inserted and slidingly travel longitudinally within the cavity until reaching a position where the console terminals are in electrical contact with the contacts on the pump unit housing.

2. A surgical irrigation system, according to claim 1, wherein said disposable pump unit includes an inlet flow tube for connecting the pump/motor module to a source of irrigating fluid, a handpiece having at least one valve for initiating the flow of irrigation liquid, the irrigation outlet tube connecting said module to said handpiece.

3. A surgical irrigation system according to claim 2, further including a flow sensing means in said console responsive to the flow of liquid in said irrigation outlet tube for starting and stopping the motor.

4. A surgical irrigation system according to claim 2, wherein said console includes means for converting an alternating current to said direct current.

5. A surgical irrigation system according to claim 2, wherein said console includes means for varying the voltage applied to said terminals.

6. A surgical irrigation system according to claim 2, wherein said pump/motor module includes a flow responsive device and said console includes a sensor responsive to said flow responsive device for turning said motor on and off.

7. A surgical irrigation system according to claim 2, wherein said console includes a control circuit for selectively applying said direct current to said terminals when the pump/motor is seated in the console.

8. A surgical irrigation system according to claim 1, wherein said pump/motor module and console include cooperating elements which prevent lateral movement of the module relative to the console.

9. A surgical irrigation system according to claim 1, wherein the contacts on the pump unit are spring biased outwardly from said housing.

10. A surgical irrigation system according to claim 1, wherein said console includes means for varying the voltage applied to said terminals.

11. A surgical irrigation system according to claim 10, wherein the means for varying the voltage applied to the terminals is a switch.

12. A surgical irrigation system according to claim 1, wherein said pump/motor module includes a flow responsive device and said console includes a sensor responsive to said flow responsive device for turning said motor on and off.

13. A surgical irrigation system according to claim 1, wherein said console includes a control circuit for selectively applying said direct current to said terminals when the pump unit is seated in the console.

14. A surgical irrigation system according to claim 1, wherein said console includes means for mounting the console on a pole.

15. A surgical irrigation system according to claim 1, wherein said console includes means responsive to the current flow to the motor for turning the motor off when the current is below a predetermined level.

16. A surgical irrigation system according to claim 1, wherein the console seat comprises an upper seat portion and a lower seat portion and each portion is adapted to receive features on the pump unit housing.

17. A surgical irrigation system according to claim 1, wherein the console includes recessed longitudinal channels to permit insertion of the module in only one orientation within the cavity and the pump unit housing includes longitudinal ramps that are configured to be received within the recessed longitudinal channels for seating the pump unit within the console cavity as the pump unit housing is inserted therein, the console terminals being formed within the recessed longitudinal channels and the contacts on the housing being formed on the longitudinal ramps of said housing and located such that when the longitudinal ramps travel longitudinally within the recessed longitudinal channels, the console terminals are placed into electrical contact with the contacts on the pump unit.

18. For use with a surgical irrigation system which includes a reusable console containing a transformer, terminals on which a direct current is produced, a seat for mechanically supporting a disposable pump unit and permitting insertion of the disposable pump unit into a cavity formed in the console, the cavity including recessed longitudinal channels to permit insertion of the disposable pump unit in only one orientation, wherein the terminals are located within the longitudinal channels and a wire operatively coupled to the console, the disposable pump unit comprising:

a pump/motor module including:

a pump, a motor for driving said pump, a housing enclosing said pump and motor, the housing including longitudinal ramps that are received within the recessed longitudinal channels for seating the pump unit within the console cavity, contacts disposed on the longitudinal ramps of said housing, the contacts being connected to said motor, and inlet and outlet flow tubes, said housing being shaped so that when the pump/motor module is placed in said console seat, the module is mechanically supported but readily disengaged from the seat, and the terminals located within the recessed longitudinal channels are in electrical contact with the contacts disposed along the ramps and connected to the motor, the longitudinal ramps traveling within the recessed longitudinal channels prior to the contacts being placed in electrical contact with the terminals, wherein the seat is shaped to support the housing of the disposable pump unit.

19. A disposable pump unit according to claim 18, further including a handpiece having at least one valve for initiating the flow of irrigation liquid connected to said outlet tube.

20. A disposable pump unit according to claim 19, further including a flow responsive device in said pump/motor module responsive to the flow of liquid in said outlet tube when said valve is open.

21. A disposable pump unit according to claim 18, wherein the cavity is open along a top and a side of the console and is configured to enclose only three sides of the module, while a front side of the module is exposed when the module is seated.

22. A disposable pump unit according to claim 18, wherein the cavity is defined by a console floor and a shelf on which a cap of the housing rests when the module is seated within the console.

23. A disposable pump unit according to claim 18, wherein reception of longitudinal ramps in the recessed longitudinal channels prevents forward and rearward motion of the module, while allowing longitudinal movement of the module within the cavity.

24. A surgical irrigation system, comprising a reusable console and a disposable pump unit comprising a pump unit housing that is separate from the console and is insertable therein, said console including a transformer for producing a direct current, terminals on which a direct current from said transformer is produced, and a seat for mechanically supporting said pump unit after insertion of the pump unit into a cavity of the console, the seat shaped to substantially support the pump unit housing and includes shelves on which the pump unit rests, the shelves being formed intermediate opposing ends of the cavity, the shelves being formed at entrances to a pair of recesses formed in the console which receive the pump unit housing and in which an electrical connection is formed between the pump unit and the console, the cavity being open along a front side thereof, the cavity being open along a longitudinal direction of the console such that the console is open along a front side thereof and is open in a longitudinal direction of the console, and a wire operatively connected to the console, said pump unit including a pump/motor module including a pump, a motor for driving the pump, and an outlet tube that is operatively coupled to the pump, said pump unit housing containing said pump and motor, and contacts on said housing electrically connected to the motor, said housing being shaped so that when the pump unit is inserted into said cavity of said console and when seated against the shelves, the pump unit is mechanically supported by the console and the console terminals are in electrical contact with the contacts on the pump unit housing connected to the motor, the pump unit being accessible and exposed along the open front side of the console to allow the pump unit to be disengaged from the console by pushing upwardly on a bottom of the pump unit.

* * * * *